United States Patent [19]
Clayman

[11] Patent Number: 5,904,679
[45] Date of Patent: May 18, 1999

[54] CATHETER WITH ELECTROSURGICAL CUTTER

[75] Inventor: Ralph V. Clayman, St. Louis, Mo.

[73] Assignee: Applied Medical Resources Corporation, Laguna Hills, Calif.

[21] Appl. No.: 08/216,512

[22] Filed: Mar. 22, 1994

Related U.S. Application Data

[63] Continuation of application No. 08/070,495, Jun. 2, 1993, abandoned, which is a continuation of application No. 07/647,472, Jan. 29, 1991, abandoned, which is a continuation-in-part of application No. 07/522,148, May 11, 1990, abandoned, which is a continuation-in-part of application No. 07/298,477, Jan. 18, 1989, abandoned.

[51] Int. Cl.⁶ .................................................. A61B 17/36
[52] U.S. Cl. ............................. 606/39; 606/45; 606/159; 606/194; 604/114
[58] Field of Search ...................... 606/7, 28, 37, 606/39, 45, 49, 159, 113, 194; 128/757, 751; 604/20, 22, 114; 600/370, 564; 607/99, 101, 113

[56] References Cited

U.S. PATENT DOCUMENTS

| | | |
|---|---|---|
| 3,435,826 | 4/1969 | Fogarty . |
| 3,467,101 | 9/1969 | Fogarty et al. . |
| 3,791,387 | 2/1974 | Itoh . |
| 3,896,815 | 7/1975 | Fettel et al. . |
| 3,910,279 | 10/1975 | Okada et al. . |
| 3,911,927 | 10/1975 | Rich et al. . |
| 3,923,065 | 12/1975 | Nozick et al. . |
| 3,982,554 | 9/1976 | Dyck . |
| 4,273,128 | 6/1981 | Lary . |
| 4,311,143 | 1/1982 | Komiya . |
| 4,325,374 | 4/1982 | Komiya . |
| 4,326,530 | 4/1982 | Fleury, Jr. . |
| 4,338,942 | 7/1982 | Fogarty . |
| 4,484,579 | 11/1984 | Meno et al. ............................. 606/194 |
| 4,503,569 | 3/1985 | Dotter . |
| 4,564,014 | 1/1986 | Fogarty et al. . |
| 4,660,560 | 4/1987 | Klein . |
| 4,669,469 | 6/1987 | Gifford . |
| 4,709,698 | 12/1987 | Johnston et al. . |
| 4,747,405 | 5/1988 | Leckrone . |
| 4,793,348 | 12/1988 | Palmaz ........................................ 606/1 |
| 4,799,479 | 1/1989 | Spears ....................................... 606/28 |
| 4,886,061 | 12/1989 | Fischell et al. .......................... 606/159 |
| 4,919,133 | 4/1990 | Chiang .................................... 606/159 |
| 4,976,711 | 12/1990 | Parins et al. .............................. 606/48 |
| 5,053,044 | 10/1991 | Mueller et al. .......................... 606/159 |
| 5,080,660 | 1/1992 | Buelna ...................................... 606/46 |
| 5,196,024 | 3/1993 | Barath . |

FOREIGN PATENT DOCUMENTS

| | | |
|---|---|---|
| 0315730 | 5/1989 | European Pat. Off. . |
| 2594322 | 8/1987 | France . |
| 2426781 | 12/1975 | Germany . |
| 938977 | 6/1982 | Russian Federation . |
| 938977 | 6/1982 | U.S.S.R. . |
| 8901800 | 3/1989 | WIPO . |

OTHER PUBLICATIONS

Banning G. Lary MD, et al., "Myocardial Revascularization Experiments Using the Epicardium", *Arch. Surg.*, 98:60–72, 1969.

Banning G. Lary, MD, "Coronary artery resection and replacement by a blood conduit", *Surgery*, 65:584–589, 1969.

Banning G. Lary, M.D., "An Epicardial Purse String Suture For Closing Coronary Arteriotomy", *Am. Surg.*, 33: pp. 213–214, 1967.

Banning G. Lary MD, et al., "A method for creating a coronary–myocardial artery", vol. 59:1061–1064, 1966.

Banning G. Lary, MD, "Method for Increasing the Diameter of Long Segments of the Coronary Artery", *Amer. Surg.*, 32:33–35, 1966.

Banning G. Lary, M.D., "Coronary Artery Incision and Dilation", *Archives of Surgery*, vol. 115, pp. 1478–1480, Dec. 1980.

Banning G. Lary, et al., "Experimental Vein Angioplasty of the Circumflex Coronary Artery", *Journal of Surg. Res.*, 17:210–214, 19.

Banning G. Lary, MD, "A Method to Create and Correct Stenosis of a Coronary Artery", *Arch. Surg.*, vol. 93, pp. 828–830, Nov. 1966.

*Primary Examiner*—Ronald Stright, Jr.
*Attorney, Agent, or Firm*—Richard L. Myers

[57] ABSTRACT

A catheter assembly which permits simultaneous dilatation and incision of tissue whereby trauma and damage to the tissue due to uncontrolled tearing is reduced or eliminated comprising an elongated tubular body having a distal end that carries a dilatation balloon and cutting element carried on the exterior of the balloon and that moves radially in concert with the exterior of the bladder as the bladder is inflated and deflated. A radiofrequency current is directed through the cutting element to incise proximate tissue. Pressure can be applied to the tissue prior to cutting to facilitate separation and subsequent to cutting to inhibit bleeding.

64 Claims, 5 Drawing Sheets

CATHETER WITH ELECTROSURGICAL CUTTER

CROSS-REFERENCE

This application is a continuation of application Ser. No. 08/070,495, filed Jun. 2, 1993, now abandoned, which is a continuation of Ser. No. 07/647,472 filed Jan. 29, 1991, now abandoned, which is a CIP of Ser. No. 07/522,148 filed May 11, 1990, now abandoned, which is a CIP of Ser. No. 07/298,477 filed Jan. 18, 1989 now abandoned. The application is further related to application Ser. No. 08/347,838, now U.S. Pat. No. 5,628,746 which is a Continuation of application Ser. No. 07/873,712, now abandoned, which in turn is a Continuation-In-Part of application Ser. No. 07/522,148, now abandoned.

TECHNICAL FIELD

The present invention relates generally to the field of surgical devices and more specifically to electrosurgical devices adapted to incise body tissue.

BACKGROUND OF THE INVENTION

In radiofrequency electrosurgical cutting a radiofrequency current is allowed to pass from an active cutting electrode through a patient's tissue and into a grounding pad or cable. The current cuts tissue at the active cutting electrode, the cutting rate being dependant on current density through the tissue in that area. With a low current density heat is generated but no cut is achieved. With a high current density fast cutting occurs.

Current density depends upon the voltage applied to the electrosurgical circuit and the series impedance or resistance to current flow of that circuit. Current density is also dependent upon the area the active cutting electrode presents to the patient's tissue. The smaller this area, the higher the current density. Since the area of the active electrode is fixed for a specific cutter, and the series impedance of the circuit is beyond the surgeon's control, the current density is typically adjusted by varying the voltage applied to the electrode. This adjustment is typically present on conventional electrosurgical generators.

The series impedance is dependent upon several factors which are outside the control of the surgeon. These factors may include the material and design of the active electrode, the type of tissue to be cut, and the location of the grounding pad relative to the cutting site. Generators used in this type of surgery have a wide range of power output to accommodate a variety of procedures and devices. For example, the generator can be adjusted to either cut tissue or to merely cauterize previously cut or torn tissue.

The objective in electrosurgical cutting is to heat the cells of the tissue so rapidly that they explode into steam leaving a cavity in the cell matrix. The heat is meant to be dissipated in the steam and not to dry out adjacent cells. When the electrode is moved and fresh tissue is contacted, new cells are exploded and the incision is made. The current utilized in electrosurgical cutting is in the radiofrequency range and operates by jumping across an air gap to the tissue. This is commonly referred to as sparking.

An explanation of electrosurgical cutting theory can be found in the FORCE 1 Instruction Manual published by Valleylab of Boulder, Colo., on Mar. 1, 1986.

An advantage of electrosurgical cutting, particularly if it is performed utilizing a cutting electrode as disclosed in application Ser. No. 07/522,254 filed May 11, 1990, now U.S. Pat. No. 5,080,660 is that overheating of adjacent tissue with accompanying desiccation and damage is limited or prevented. Thus, this procedure provides a clean cut without damage to adjacent tissue. A clean controlled cut is particularly desirable to assure that tearing does not occur in a direction away from the desired orientation of the cut.

Dilatation catheters are used to dilate body vessels, orifices and conduits such as an artery narrowed by atherosclerotic plaque or a urethra constricted by an enlarged prostate. These catheters basically consist of an elongate cannula having an inflatable non-extensible balloon or bladder at or near its distal end. A guide wire or other axial support means is often included to improve the torque control or "steerability" of the catheter.

The major advantage of using a dilatation catheter instead of conventional surgery is that it is less invasive. Nevertheless, the dilatation processes of the past can also result in significant trauma. As the elastomeric bladder expands, it exerts pressure on the surrounding tissue, causing the tissue to compress, deform and expand. The tissue, of course, has an inherent limit of deformability. When the dilation pressure causes the tissue to deform beyond that limit, the tissue tears apart, often to form a jagged wound. A principal object of the present invention is to provide a dilatation catheter that permits tissue to be stressed, even beyond its limit of deformability, without experiencing uncontrolled tearing and the undesirable conditions associated therewith.

U.S. Pat. No. 4,747,405 issued to Leckrone on May 31, 1988, U.S. Pat. No. 4,669,469, issued Jun. 2, 1987 to Gifford, III., et al., and PCT/US 86/02617 application of Leckrone, published Jun. 16, 1988, are each concerned with atherecotomy devices wherein a balloon is used to position an opening in a casing about an obstruction such as plaque. The balloon does not carry a cutting element to incise tissue but does carry means for disintegrating the plaque which is generally entrapped within a hole in the casing. The balloon basically positions the hole in the casing up against and about the plaque. Thus, the balloon is not symmetrically located within the blood vessel, an outward cutting element is not present, and the blood vessel is not torn by the dilation force.

U.S. Pat. No. 4,799,479, issued Jan. 24, 1989 to Spears, shows use of a balloon to open up an artery and then utilizes a laser, heated wire mesh, or the like, to heat up blood trapped between the media and the plaque so that dilation will be maintained and so that a smooth wall will result.

U.S. Pat. No. 4,273,128, issued Jun. 16, 1981 to Lary, teaches the use of a balloon with a knife blade, or a series of knife blades, longitudinally distally removed from the balloon.

Soviet Patent 599802 published in 1976 utilizes a balloon which is located within a tube. When the balloon is extended this forces a cutting element through a window in the tube to accomplish fenestration. Balloon pressure is not exerted against body tissue as the balloon is expanded within the tube.

German Patent 3,402,573 is concerned with a single lumen multi-purpose catheter having an extensible elastic balloon with a cutting facility for treatment of stenosis. This patent utilizes three balloons of equal size at the distal end of the catheter. Each elastomeric balloon carries small cutter elements which extend in the longitudinal direction and which are held in a trough made of hard rubber or plastic. Prior to use the cutters lie hidden in longitudinal slots of the relatively thick wall of the one-lumen catheter. Threads anchor the plate when the balloons are inflated thereby limiting the degree of penetration of adjacent plaque and possibly tissue.

U.S. Pat. No. 4,484,579, issued to Meno, et al. on Nov. 27, 1984, is concerned with a commissurotomy catheter which serves for separating fused heart valve leaflets. The device includes four balloons carried by a single catheter structure. In use the device fits through the valve with two balloons on each side of the valve. A nylon or similar string is attached between the pairs of balloons on each side of the valve. The balloons can be alternately expanded and contracted thereby causing the strings strung between each pair of balloons to saw or pulsate into fused portions of the heart valve leaflets and separate them. The actual cutting portion of the string is not carried on the exterior of the balloons.

The above-mentioned patents do not make use of an electrosurgical or radiofrequency cauterizing or cutting element. Nor do the above patents either suggest or show any advantages for utilizing an inextensible bladder or balloon, i.e., a balloon which is not elastomeric (or elastic) and which can be inflated to only a selected shape and volume. Furthermore, the above discussed patents are not concerned with a radially symmetrically, generally cylindrical in shape when expanded, balloon which extends longitudinally along a body passage and a cutting element which extends longitudinally along and generally parallel to the balloon, which balloon creates a substantially uniform tangential tension in tissue being cut, and which cutting element at the same time performs the necessary cutting whereby a clean longitudinally extending incision results and uncontrolled tearing of the tissue does not occur.

The present invention is directed to overcoming one or more of the problems as set forth above.

SUMMARY OF THE INVENTION

A catheter assembly is used to deploy a cutting element such as an electrosurgical cutter, into a body passage, such as a vessel, orifice or other body conduit. A dilatable balloon disposed at the distal end of the catheter provides means for moving the cutting element outwardly of the catheter toward the tissue to be cut. After the balloon has been dilated and the cutting element is disposed in proximity to the tissue, the element can be activated, for example with a radiofrequency signal, to cut the tissue. Then the signal can be reduced in magnitude to cauterize the cut tissue prior to deflating the balloon. Once the balloon is deflated and the cutting element retracted into proximity to the catheter, the lower profile of the catheter will permit withdrawal from the passage.

In accordance with an embodiment of the invention a dilatation catheter assembly comprises in combination: an elongated tubular body having a distal end carrying a radially dilatable inextensible elongate member adapted to be positioned longitudinally along a body conduit and to dilate in a radially symmetrical manner and exert pressure on surrounding body tissue to provide a substantially uniform tangential tension therein; means for dilating the dilatable member to a relatively constant inextensible volume and a cutting element carried on the exterior of the dilatable member that moves radially in concert with the exterior of the dilatable member and is adapted to incise said tissue, thereby reducing damage to said tissue from dilation forces.

In accordance with another embodiment of the invention a dilatation catheter assembly comprises, an elongated tubular body having a distal end carrying a radially dilatable member adapted to be positioned in a body conduit and to exert pressure on surrounding body tissue; means for dilating the dilatable member; and an electrosurgical cutting element carried on the exterior of the dilatable member that moves radially in concert with the exterior of the dilatable member and that is adapted to incise the tissue, thereby reducing damage to the tissue from dilation forces.

In another aspect of the invention, the catheter is particularly adapted for enlarging the diameter or other cross-sectional dimension of a body passage, such as a vessel orifice or other body conduit. A conduit of particular interest is the prostatic urethra which in the case of male patients is commonly restricted by the inward growth of the prostate gland which surrounds the urethra. Such restriction often inhibits urination resulting in the discomfort associated with frequency, urgency and control. Various attempts have been made to dilate the prostatic urethra but success has been considerably limited in terms of both efficacy and longevity.

Accordingly, another aspect of the invention is a method for dilating a body conduit, vessel or orifice comprising the steps of inserting thereinto a dilatation catheter assembly comprising an elongated tubular body having a distal end carrying a radially dilatable inextensible member adapted to be positioned in a body conduit and to dilate in a radially symmetrical manner and to exert pressure on surrounding body tissue to provide a substantially uniform tangential tension therein, and a cutting element carried on the exterior of the dilatable member; dilating the inextensible dilatable member to an extent that causes the tissue to be simultaneously stressed by the dilatable member and incised by the cutting member; radially contracting the dilatable member to cause the dilatable member and cutting element to disengage the tissue; and withdrawing the dilation catheter assembly from the conduit, vessel or orifice.

Still another aspect of the present invention is a method for dilating a body conduit, vessel or orifice. This method comprises inserting thereinto a dilation catheter assembly comprising an elongate tubular body having a distal end carrying a radially dilatable member adapted to dilate and exert pressure on surrounding body tissue and an electrosurgical cutting element carried on the exterior of the dilatable member; simultaneously dilating the dilatable member to an extent that causes the tissue to be stressed by the dilatable member and activating the electrosurgical cutting element such that the tissue is simultaneously stressed by the dilatable member and incised by the cutting element; discontinuing activation of the electrosurgical cutting element; radially contracting the dilatable member to cause the dilatable member and cutting element to disengage the tissue; and withdrawing the dilation catheter assembly from the conduit, vessel or orifice.

BRIEF DESCRIPTION OF THE DRAWINGS

The invention will be better understood with reference to the drawings wherein like numbers denote like parts and wherein.

BEST MODE FOR CARRYING OUT INVENTION

Figure 1:
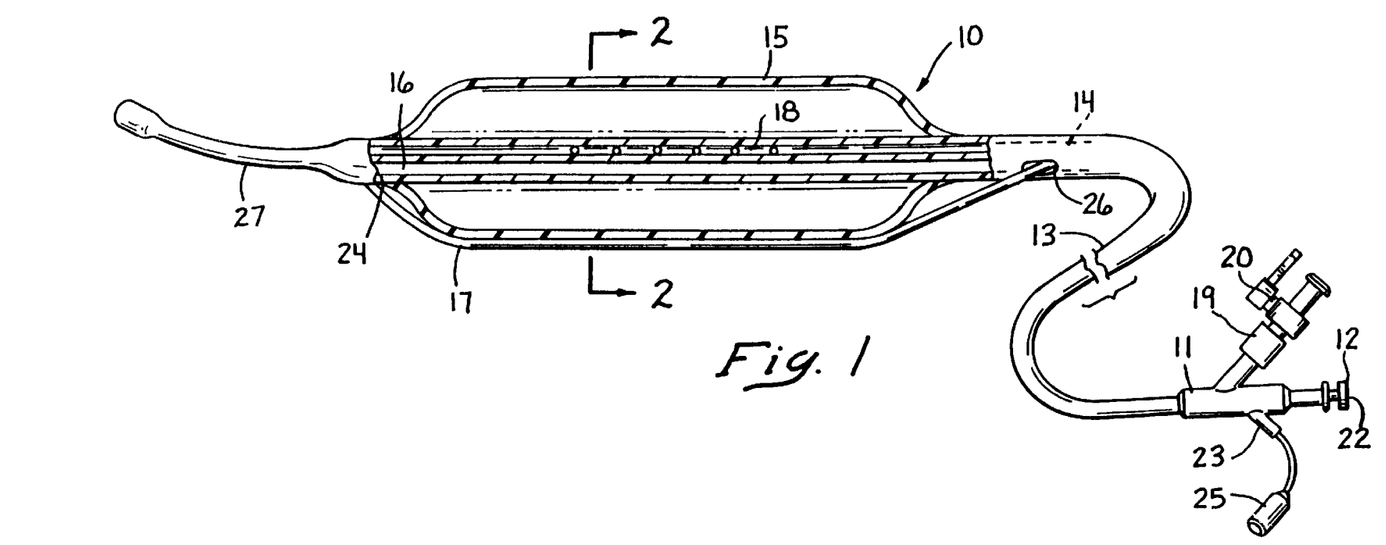
FIG. 1 is a partly cross-sectional, isometric view of one embodiment of the invention catheter.

FIG. 1 depicts a dilatation catheter assembly, generally designated 10, that may be used for dilating a body vessel or conduit, such as a ureter or urethra, to treat a blockage or other obstruction. The main elements of catheter assembly 10 are: an adapter 11 that defines the proximal end 12 of the assembly 10 and a site for various ports to the assembly 10; a catheter body 13 having a triple lumen 14 (FIG. 2); an inflatable balloon or bladder member 15; a stiffening guide wire or stylet 16 that extends longitudinally within one of the three lumens 14 of the catheter body 13; and a cutting element or electrode 17, preferably a radiofrequency cutting element 17 activatable by a radiofrequency power source 21. The electrosurgical cutting element 17 is in the nature of a wire which extends generally parallel to the longitudinally-.extending inflatable bladder 15.

In use, the bladder 15 is inserted into a body conduit vessel or orifice to a location where a surgical cut is required. The bladder 15 is then inflated (an inextensible bladder is generally used) with radiofrequency current being passed through the cutting element 17. This leads to the wire being moved outwardly and incising adjacent tissue in that direction.

Figure 2:
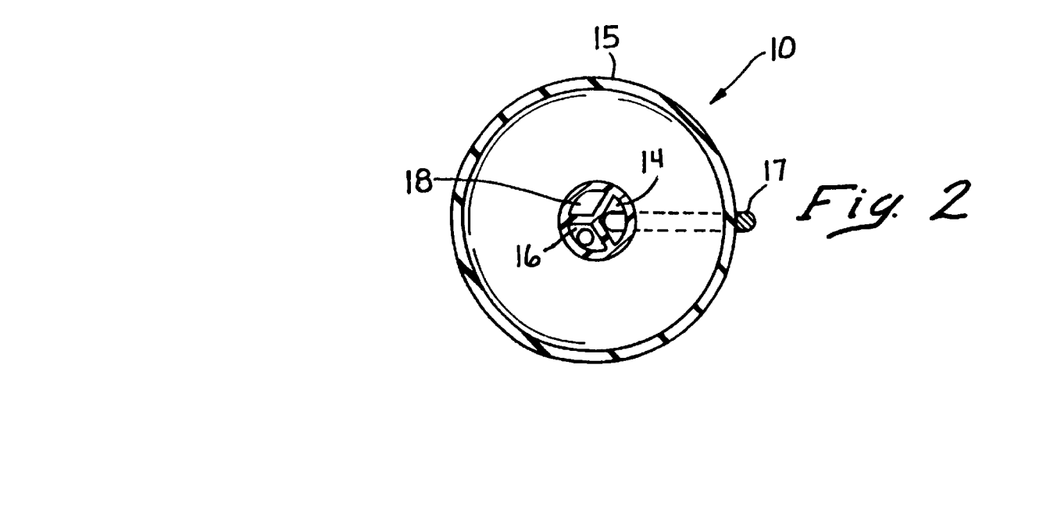
FIG. 2 is a cross-sectional view taken along line 2—2 of FIG. 1.

The material used for the wire can be any of the materials currently used for electrosurgical cutting. For example, the wire can be made of stainless steel or tungsten. As illustrated in FIG. 2 herein, one of the three lumens 14 serves as an inflation/deflation passageway 18, a second lumen carries the guidewire or stylet 16 and serves as a drainage/infusion passageway, and a third lumen carries the cutting element 17. In accordance with the teachings in previously mentioned patent application Ser. No. 07/522,254, now U.S. Pat. No. 5,080,660, a sheath surrounding the cutting element 17 can be provided with a slit facing away from the bladder 15.

In accordance with the present invention the inflatable balloon or bladder member 15 is preferably of the inextensible or constant volume variety, that is it can, when expanded, assume only a specific size and shape. Thus, the balloon member 15 cannot extend or bulge longitudinally within the body conduit beyond its predetermined diameter or length. Since a nondistensible balloon member 15 cannot extend longitudinally, as can elastic or elastomeric balloons, it must exert the force caused by inflation of the balloon member 15 radially against an enclosing body conduit or the like. In contrast, if an elastic or elastomeric balloon is expanded within a body conduit which has one portion particularly narrowed and particularly resistant to expansion, the balloon will simply elongate rather than acting radially outwardly against the constriction.

In accordance with the present invention it is preferred to utilize a radiofrequency cutting element 17 for a number of reasons. One reason is that a radiofrequency cutting element 17 will not perform any cutting unless and until it is activated by passing a radiofrequency current through it. As a result, accidental cuts cannot be made away from the area where cutting is desired. And second, with proper control, cutting can be very sharply defined leading to a clean incision without tearing. This radiofrequency cutting or cauterizing technique can, thus, provide significant advantages over the use of prior art cutters in an apparatus of the nature disclosed herein.

In accordance with the present invention the balloon member 15 generally extends longitudinally along the body conduit and is generally symmetrically placed and expandable therein. In this manner, as the balloon member 15 is expanded, it exerts a substantially equal tangential tension upon the tissue defining the body conduit. This results in a very clean incision which extends generally parallel to the balloon member 15. In this manner the incision can be positioned longitudinally along the body cavity rather than at an axial angle as might be the case if the tangential tension in the body conduit were not substantially uniform.

In accordance with the most preferred embodiment of the present invention, the cutting element 17 is a radiofrequency cutting element and is disposed parallel to the bladder member 15. This bladder member 15 extends longitudinally along the body conduit, is constructed of an inextensible non-elastic, non-elastomeric material and is symmetrically placed within the body cavity so that on expansion it exerts a substantially uniform tangential tension upon the tissue defining the body cavity. This configuration achieves many of the advantages associated with the present invention.

The adapter 11 serves as a site for a bladder inflation/ deflation port 19 that is attached to a source of inflation medium (not shown) for inflating the bladder member 15, or to a suction source (not shown) for deflating the bladder member 15. Port 19 has a valve 20 for regulating the inflation medium or suction, as the case may be. Port 19 connects into the proximal end of an inflation/deflation passageway 18 that extends from the port 19 to the bladder member 15. The adapter 11 also serves as a site for the drainage tube inlet/outlet port 22 and a cutting element port 23. The drainage port 22 is connected to the proximal end of the lumen that carries the guide wire or stylet 16. The drainage port 22 may serve as a site for removing fluid from the lumen or as a site for infusing fluid into the lumen.

The distal end of the catheter body has a series of drain holes 24 to facilitate flushing the lumen with fluid or voiding the bladder member 15. A "banana plug" cutting element connector 25 is affixed to the end of the cutting element port. The cutting element 17 extends from the connector 25 through the lumen of the catheter body 13, exits therefrom via an aperture 26, and continues along the exterior of the bladder member 15.

The cutting element 17 can consist of a thin wire which has an external incising edge that faces outwardly from the bladder member 15. Alternatively, the cutting element 17 may be a sharp edge, beam, or, more preferable, a radiofrequency cutting or cauterizing element 17. The element 17 and bladder member 15 are constructed such that the cutting element 17 is carried on the exterior of the bladder member 15 (at least when the bladder member is inflated) but is not capable of incising the bladder member 15.

If desired, the portion of the exterior of the bladder member 15 that is exposed to the cutting element 17 may carry a protective cover (not shown) to further guard against the bladder member 15 being incised by the cutting element 17. The cutting element 17 may be carried at a predetermined spacing from the bladder surface or directly on the surface. When carried on the surface the cutting element 17 may be an integral part of the surface or may be attached to the surface. In a preferred embodiment, the cutting element 17 is manually extendable or retractable via the connector 25 into and out of the catheter body 13.

For use in urethral dilatation the distal end of the assembly 10 includes a coudet tip 27. Such structure may not be necessary or desirable for dilating other conduit/orifices. For urethral dilation, the assembly 10 may optionally include another lumen and "Foley" type balloon (not shown) distally of the dilatation bladder member 15 to anchor the catheter in the bladder neck of the human body and thereby facilitate correct positioning of the dilatation bladder member 15. This has the further advantage of minimizing the possibility of migration and displacement of the assembly 10. One or more of the catheter assembly components may be made of radiopaque materials to facilitate the visualization of the assembly 10 by the physician during placement of the assembly 10 in the body vessel/conduit.

The typical surgical procedure in which the catheter assembly 10 is employed, involves the following steps. Normally a cytoscope is first inserted into the vessel/conduit/orifice to be dilated. Calibration devices may be inserted through the cytoscope to facilitate measuring the extent of the vessel/conduit/orifice being dilated. The dilatation catheter of FIG. 1 is then inserted to the desired depth in the vessel/conduit and positioned using fluoroscopic and/or x-ray techniques.

Once in position, the bladder member 15 is inflated. Such inflation causes the cutting element 17 to move radially outwardly as the bladder surface expands radially until the cutting element 17 contacts the surrounding tissue. As used herein the term "tissue" is intended to include, without limitation, normal tissue, neoplastic tissue (tumors) or an obstruction such as plaque. In accordance with a preferred embodiment of the invention the bladder member 15 is nondistensible.

Continued radial expansion of the bladder member 15 positions the cutting element 17 and causes the bladder member 15 to exert pressure on the tissue thereby subjecting the tissue to a substantially uniform tangential tension. Then a radiofrequency current can be passed through the cutting element 17.

This combined cutting and dilating action results in the tissue being expanded without being torn due to a buildup of excess stresses within the tissue. Instead, the tissue is cut in a clean, concentrated, generally longitudinal fashion by the cutting element 17 and the dilatation does not uncontrollably tear the tissue and cause excessive trauma and bleeding. The inflated bladder member 15 provides the additional benefit of acting as a tamponade to reduce bleeding.

After the vessel/conduit/orifice tissue is incised and dilated, and the blockage/obstruction is relieved, the power through the radiofrequency cutting element 17 is discontinued. Then the bladder member 15 can be deflated by operation of the inflation/deflation port valve 20. Deflation of the bladder member 15 permits a simultaneously radial retraction of the cutting element 17 out of contact with the tissue. As the bladder member 15 is deflated the cutting element 17 may be retracted via the connector 25. If desired, the cutting element 17 may be retracted prior to complete deflation of the bladder member 15 and/or the bladder member 15 reinflated and left in place to act as a tampon. Alternatively, the catheter can be withdrawn from the vessel/conduit altogether.

FIGS. 3–6 depict another dilatation catheter assembly of the invention, designated generally by the reference numeral 29. Only the distal end of the assembly 29 is shown. The adapter(s), as well as the various inflation/deflation ports are not shown for convenience. The distal end of the catheter is defined by a closed end catheter tube 32 which carries an inflatable, preferably inextensible, bladder member 33 on its exterior. The lumen 34 of the tube 32 is connected to the source of inflation fluid pressure/suction, as the case may be. The tube 32 has a radial aperture 35 that opens into the lumen 36 of the bladder member 33. A pair of expandable ring-shaped members 37, 38 extend around the exterior of the bladder member 33 near the distal and proximal ends thereof. One or more cutting elements 39 are affixed between the rings so that they extend longitudinally and outwardly therefrom.

Figure 3:
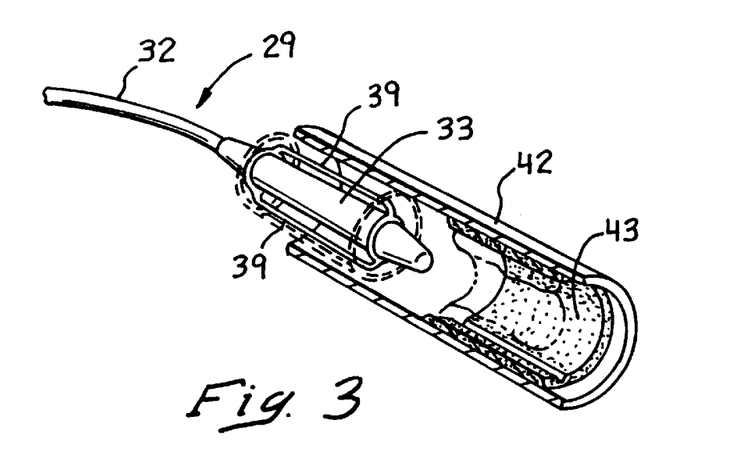
FIG. 3 is a perspective, schematic, sectional view of a portion of another embodiment of the invention illustrating the catheter positioned within a body conduit.
Figure 4:
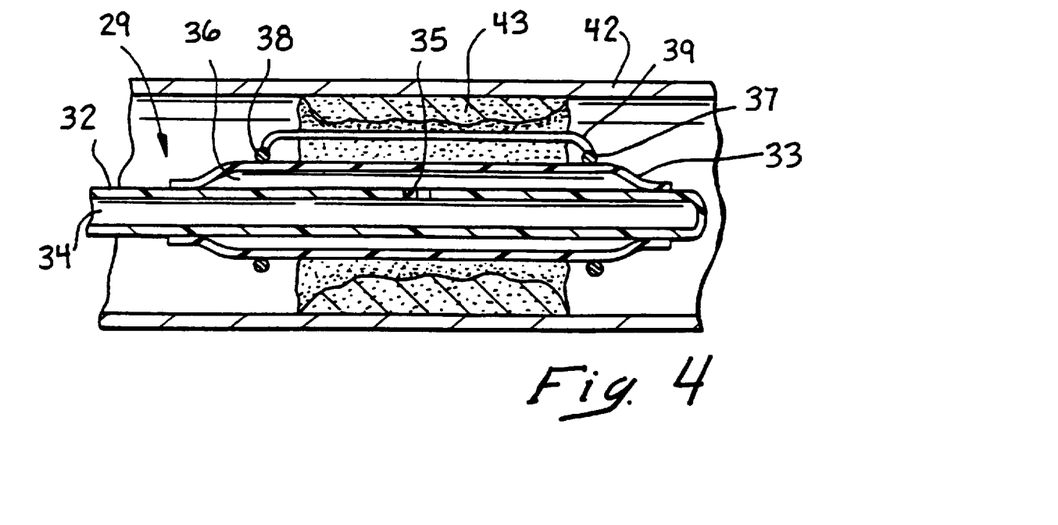
FIG. 4 is a sectional, side view of the embodiment of FIG. 3 in a deflated state.
Figures 5, 6:
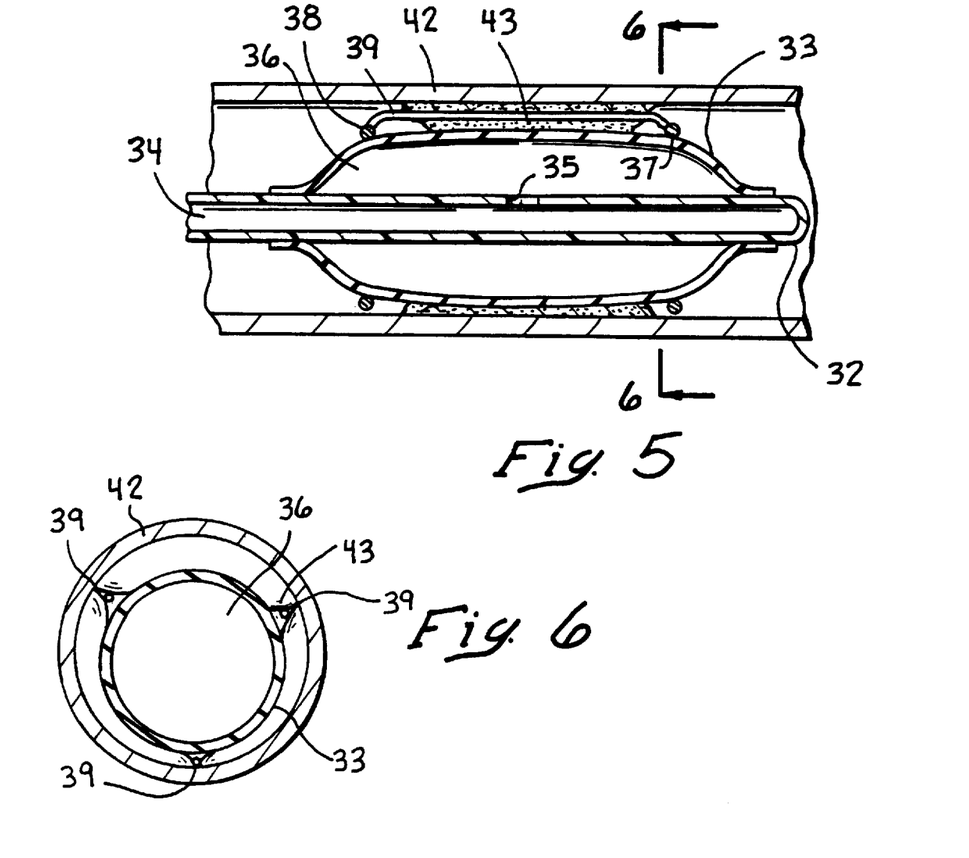
FIG. 5 is a sectional side view of the embodiment of FIG. 3 in an inflated state.
FIG. 6 is a cross-sectional view along line 6—6 of FIG. 5.

FIG. 3 (in solid line) and FIG. 4 show both the assembly 29 in its deflated state positioned within a vessel 42 partially occluded by an obstruction 43. In order to inflate the bladder member 33, pressurized fluid is passed through catheter tube lumen 34 and aperture 35 into the bladder lumen. Inflation of the bladder member 33 in turn causes the ring members 37, 38 to expand and move the cutting element(s) 39 radially outward. FIGS. 3 (phantom line), 5, and 6 show the bladder member 33 in an inflated state with the cutting element 39 incising the obstruction.

Figure 7:
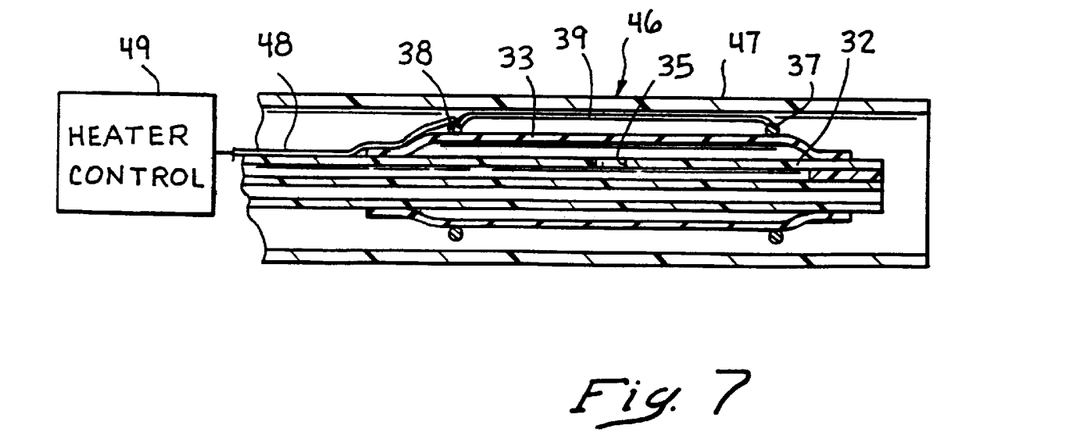
FIG. 7 is a sectional, elevational view of another embodiment of the invention.

FIG. 7 shows yet another dilatation catheter assembly, generally designated 46, of the invention. The assembly 46 is shown in its deflated state. This assembly 46 is similar in structure to assembly 29 except that the assembly 46 is housed within a sheath or introducer 47 and a cauterizing element 48 is connected to the cutting element 39. The sheath permits the assembly 46 to be introduced into the vessel in an unexposed manner, ejected from the end thereof for use, and retracted back into the sheath 47 after use. The ejection and retraction may be achieved by relative longitudinal movement of the sheath 47, assembly 46, or both.

A heating element 49 permits the cutting element (which in this instance must be made of a heat conducting material) to be heated to a temperature which allows the tissue to be both incised and cauterized. The heating element is connected to a heat source/control, schematically shown at 49. As an alternative the cutting element 39 can be a radiofrequency cutting element and cauterization will result along with the cutting. Also, following cutting a reduced power radiofrequency signal can be passed through cutting element 39 to accomplish further cauterization. In such an embodiment, the heat source control 49 would be replaced by a radiofrequency signal generator.

Figure 8:
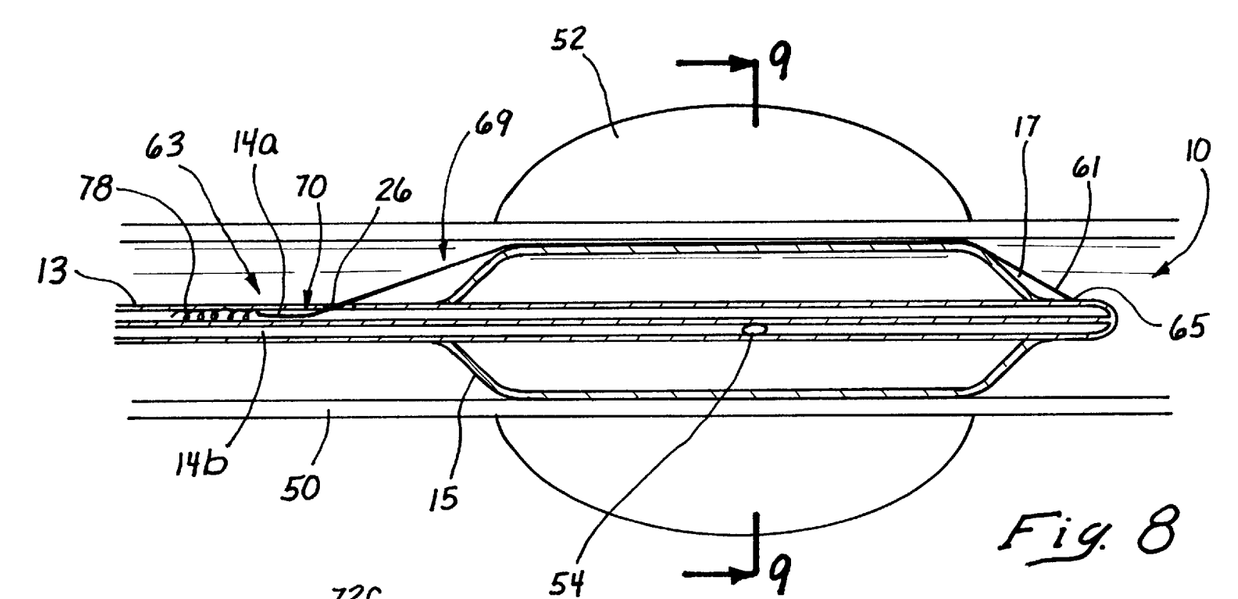
FIG. 8 is an axial cross-sectional view of a further embodiment of the invention illustrating the catheter disposed in the urethra in proximity to the prostate gland.

The catheter assemblies associated with the present invention are of particular advantage when used to enlarge a body passage such as a vessel, or orifice, or other body conduit. As illustrated in FIG. 8, this passage or body conduit may include a urethra 50. In the case of a male patient, the urethra 50 is surrounded by a prostate gland 52 which has a relatively thick, inflexible outer layer of tissue. The interior tissue forming the prostate gland 52 tends to expand or grow with age, and the relatively thick outer tissue forces this growth inwardly where it tends to restrict the passage formed by the urethra 50.

In a procedure for enlarging the prostatic urethra 50, the catheter 10 (including at least a pair of lumens 14a and 14b) can be inserted into the urethra 50 with the balloon 15 positioned in a deflated state within the prostate 52. In this particular catheter illustrated in FIG. 8, the electrosurgical cutting element 17 is disposed in outlying relationship with respect to the balloon 15 between the balloon 15 and the wall of the urethra 50. The cutting element 17 includes a first end 61 and a second end 63. The first end 61 is fixed to the catheter at a point 65 which in this embodiment is located at the distal end of the catheter 10. From this point 65, the cutting element 17 extends outwardly of the balloon 15, through the aperture 26 and into the lumen 14a of the catheter 10. Within the lumen 14a, the cutting element 17 is attached to one end of a spring 78 the other end of which is fixed to the catheter body 13. The cutting element 17 is energized with radiofrequency power which is transmitted through the spring 78 into the cutting element 17. From the forgoing description it is apparent that the cutting element 17 includes portions 69 which are disposed exteriorly of the catheter body 13, and portions 70 which are disposed interiorly of the catheter body 13.

In accordance with a preferred method the balloon 15 is inflated by introducing a fluid into the lumen 14b which then exits the lumen 14b through a port 54 beneath the balloon 15. As the fluid inflates the balloon 15, the cutting element 17 is carried outwardly against the force of the spring 78 into proximity with the wall of the urethra 50.

In a preferred embodiment the balloon 15 is symmetrical about a longitudinal axis which is aligned with the longitudinal axis of the catheter 10. As the balloon 15 expands, it exerts a generally equal pressure against the wall of the urethra 50 thereby placing this tissue in tension.

When the electrosurgical element 17 is activated by the radiofrequency signal, a current of high density is passed through the cells of the urethra 50 which are in close proximity to the element 17. By activating the cutting element 17 the cells are vaporized, incised, or otherwise cut along the element 17.

Figure 9:
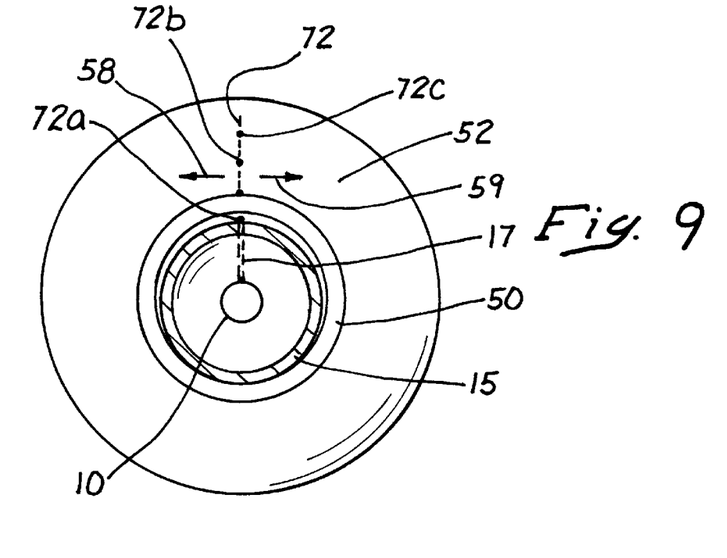
FIG. 9 is a radial cross-sectional view taken along lines 9—9 of FIG. 8.

The tension in these cells tends to create forces which extend tangentially of the balloon 15 as shown by arrows 59 and 58 in FIG. 9. As previously adjacent cells are cut, they are separated by these tangential forces so that the circumference and hence the diameter of the urethra 50 is increased. As the balloon 15 is further inflated, new uncut tissue is brought into proximity to the cutting element 17 which continues to cut the tissue along a line, such as the dotted line 72 which extends generally radially of the catheter 10.

Figure 10:
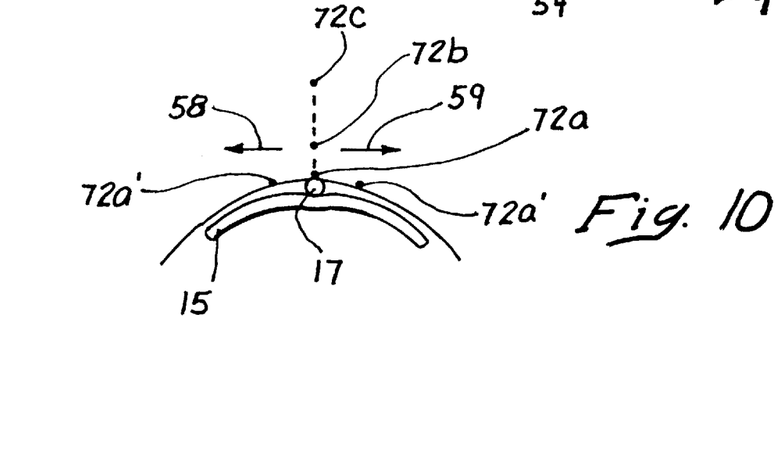
FIG. 10 is an axial cross-sectional view similar to FIG. 9 illustrating the separation of cut tissue.

In FIG. 9, a progression of points along the radial cut line 72 are designated 72a, 72b, and 72c. In FIG. 10 the tangential forces illustrated by the arrows 58 and 59 are shown to have separated the two portions of cut tissue at the point 72a and these points have moved outwardly in opposite directions as shown by the points 72a'.

As the cutting progresses, it may be advantageous to further inflate the balloon 15 in order to maintain the pressure and tangential forces required for separating the cut tissue.

The radiofrequency electrical power delivered to the cutting element 17 can be provided in different forms depending on the result desired. For example, a continuous low amplitude power can be provided to facilitate cutting of the tissue while a pulsed high amplitude power can be provided to enhance cauterization of the tissue. In practice, these different forms of power may be blended to provide for different ratios of cutting and cauterizing. Ultimately the radiofrequency power is completely discontinued to halt any further cutting or cauterizing of the tissue.

Even after cutting and cauterizing have been stopped, it may be desirable to maintain or even increase the pressure in the balloon 15 in order to provide a tamponade for inhibiting bleeding in the region of the cut cells. Ultimately the balloon can be deflated to permit the cutting element 17 to move radially away from the cut tissue into proximity with the catheter body 13.

Figure 11:
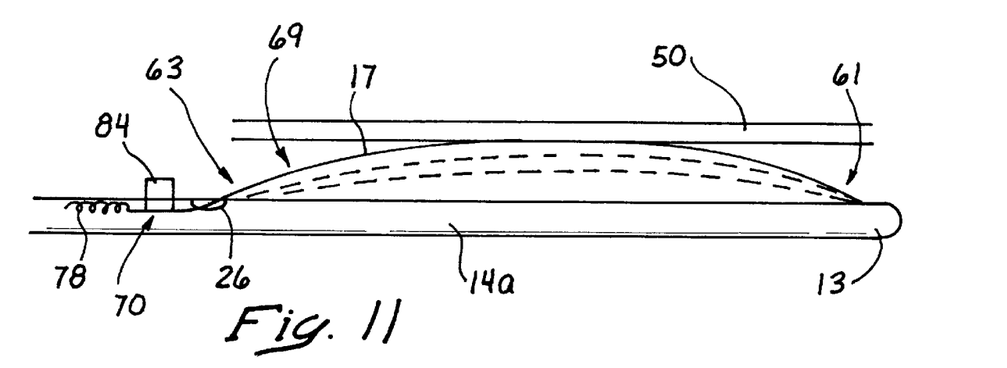
FIG. 11 is an axial cross-section view of a further embodiment of the invention including finger tab means for advancing the cutting element into proximity with the tissue.
Figure 12:
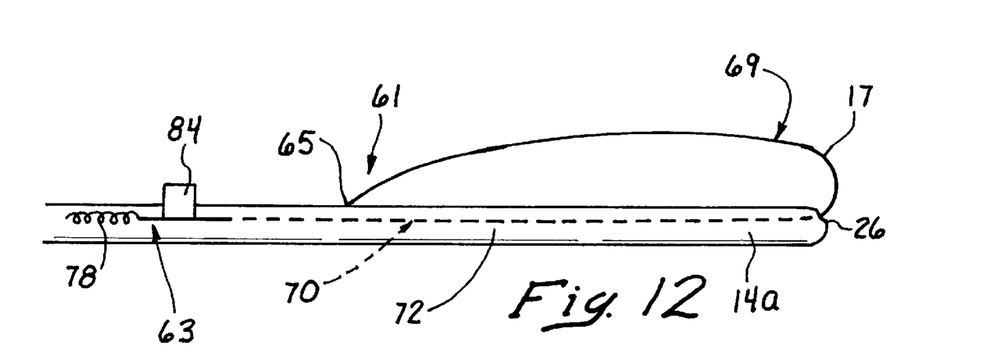
FIG. 12 is an axial cross-sectional view of a further embodiment of the invention wherein the cutting element is fixed to the catheter at a location proximal to the distal end of the catheter.

The embodiments of FIGS. 11 and 12 differ from the foregoing description in that the catheter 10 is not provided with a balloon 15. Rather, the means for advancing the cutting element 17 into proximity with the tissue, comprises a finger tab 84. This tab 84 engages the cutting element 17 preferably through a slot in the body 13 of the catheter. As the tab 84 is moved distally of the catheter 10, the cutting element 17 passes through the aperture 26 to increase the length of the exterior portions 69 relative to the interior portions 70. By increasing the length of the exterior portions 69, the cutting element 17 tends to move outwardly, radially into proximity with the urethra 50.

As the tab 84 moves distally of the catheter 10, the exterior portions 69 of the cutting element 17 assume progressive positions having a particular configuration. In most cases, this particular configuration will at least be arcuate. In FIG. 11 wherein the aperature 26 is disposed proximally of this exterior portion 69, the particular configuration tends to be parabolic. Thus each of the progressive positions of the exterior portions 69 define a parabola. In other embodiments, this particular configuration may be ovoid.

In FIG. 12, wherein the aperature 26 is disposed distally of the exterior portions 69, the particular configuration tends to take the shape of one side of a heart. Each of these configurations may have a particular advantage in the context of a particular operative procedure.

After the catheter 10 has been positioned, and the cutting element 17 has been operationally deployed into contact with the tissue, the element 17 can be activated in the manner previously discussed. When the tissue has been cut thereby enlarging the circumferential dimension of the passage or cavity, the cutting element i7 can be withdrawn from proximity to the tissue into compliance with the catheter body 13. In the embodiments of FIGS. 11 and 12, this is accomplished by moving the finger tab 84 proximally thereby drawing the cutting element into the lumen 14a of the catheter 10. By moving the finger tab 84 proximally of the catheter 10, the cutting element 17 is drawn through the aperture 26 thereby decreasing the length of the exterior portions 69 relative to the interior portions 70.

In all of these preferred embodiments, both those with the balloon 15 and those with the finger tab 84, the cutting element 17 includes the interior portions 70 which are disposed in the lumen 14a and the exterior portions 69 which are disposed outside of the catheter body 13. Either the balloon 15 or the finger tab 84 provides means for increasing the length of the exterior portions 69 so that the cutting element 17 is moved radially outwardly into contact with the tissue. In both cases, the cutting element 17 moves radially into proximity with the catheter body 13 when the radial force of the balloon or the distal force on the finger tab 84 are relieved. In both cases, the spring 78 provides a proximal tension on the cutting element 17 decreasing the length of the exterior portions 69 while increasing the length of the interior portions 70.

In the embodiment of FIG. 8, the aperture 26 is disposed proximally of the point 74. However, in the embodiment of FIG. 12, the aperture 26 is disposed at the distal end of the catheter 10 so that the point 74 is disposed proximally of the aperture 26. In this embodiment, the cutting element 17 is bent back on itself through the aperture 26. Nevertheless, these embodiments function similarly in that the cutting element moves radially, outwardly as its interior portion 72 are advanced distally in the catheter 10.

While the invention has been described in connection with specific embodiments thereof, it will be understood that it is capable of further modification, and this application is intended to cover any variation, uses, or adaptions of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. A method for dilating a non-vascular body conduit, comprising:
   inserting into the non-vascular conduit a dilation catheter assembly comprising an elongate tubular body having a distal end carrying a radially dilatable member adapted to be positioned in the conduit and to exert pressure on surrounding body tissue to provide a substantially uniform tangential tension in the tissue, and a cutting element carried on the dilatable member;
   dilating the dilatable member to simultaneously stress the tissue and engage the tissue with the cutting element;
   electrically activating the cutting element;
   incising the stressed tissue with the cutting element;
   radially contracting the dilatable member to cause the dilatable member and cutting element to disengage the tissue; and
   withdrawing the dilation catheter assembly from the conduit.

2. The method of claim 1 wherein the cutting element is a radiofrequency cutter and the method further including the steps of:
   passing a radiofrequency current through the cutter during the dilating of the dilatable member; and,
   discontinuing the radiofrequency current during the radial contracting of the dilatable member.

3. The method of claim 2 wherein the step of passing the radiofrequency current includes the steps of:
   introducing a radiofrequency signal into the cutting element to cut the tissue; and
   reducing the power of the radiofrequency signal to cauterize the cut tissue.

4. The method of claim 1 including the step of cauterizing the tissue with the cutting element.

5. A method for enlarging the diameter of a ureteral passage defined by body tissue, comprising:
   inserting into the ureteral passage a catheter having a catheter body, a cutting element in the form of an elongate wire, and means for advancing the cutting element laterally of the catheter body;
   advancing the cutting element into proximity with the tissue; and
   electrically activating the cutting element to cut the tissue and enlarge the diameter of the ureteral passage.

6. The method recited in claim 5 wherein after the activating step, the method further comprises the steps of stretching the tissue defining the ureteral passage in order to enlarge the ureteral passage.

7. The method recited in claim 6 further comprising the step of pressurizing the cut tissue to inhibit bleeding of the tissue.

8. The method recited in claim 7 further comprising the steps of:
   deactivating the cutting element;
   retracting the cutting element into proximity to the catheter body; and withdrawing the catheter from the ureteral passage.

9. The method recited in claim 7 wherein during the providing step, the catheter is provided with an inflatable balloon and during at least one of the advancing, stretching, and pressurizing steps, the method further comprises the step of inflating the balloon.

10. The method recited in claim 5 wherein after the activating step, the method further comprises the step of advancing the cutting element into proximity with previously uncut tissue.

11. The method recited in claim 5 wherein during the activating step the tissue is cut into two portions and the method further comprises the step of separating the two cut portions of the tissue to expose uncut tissue to the cutting element.

12. The method recited in claim 5 wherein prior to the activation step the method further comprises the step of stretching the tissue in proximity to the cutting element.

13. A method for enlarging the diameter of a passage defined by body tissue and having a longitudinal axis, comprising:
   inserting into the passage a catheter having an inflatable balloon and a cutting element in the form of an electrosurgical wire disposed in contact with the outer surface of the balloon;
   inflating the balloon to move the cutting element into proximity with the body tissue;
   activating electrically the cutting element to cut the body tissue in only a substantially axial direction;
   deflating the balloon to withdraw the cutting element from proximity with the body tissue; and
   withdrawing the catheter from the passage.

14. The method recited in claim 13 wherein prior to the deflating step the method further comprises the step of advancing the cutting element into proximity with previously uncut tissue.

15. The method recited in claim 14 further comprising the step of repeating the activating step.

16. The method recited in claim 13 wherein prior to the activating step the method further comprises the step of stretching the body tissue.

17. The method recited in claim 13 wherein subsequent to the activating step the method further comprises the step of pressurizing the cut tissue to inhibit bleeding.

18. The method recited in claim 13 wherein prior to the deflating step the method further comprises the step of deactivating the cutting element to discontinue cutting the body tissue.

19. The method recited in claim 13 wherein during the deflating step the method further comprises the step of automatically retracting the cutting element from proximity with the body tissue.

20. A method for enlarging the diameter of a passage defined by body tissue, comprising:
   inserting into the passage a catheter having a wall defining a lumen extending between a distal end of the catheter and a proximal end of the catheter, and an electrosurgical wire having first portions disposed exteriorly of the catheter and second portions disposed interiorly of the catheter, the wire including a first end fixed to the catheter and a second end movable within the lumen of the catheter to vary the length of the first portions of the wire relative to the length of the second portions of the wire;

moving the second end of the wire distally within the lumen of the catheter to increase the length of the first portions of the wire and thereby move the first portions laterally of the catheter wall into proximity with the tissue;

activating the electrosurgical wire to cut the tissue in proximity to the wire; and moving the second end of the wire proximally within the lumen of the catheter to decrease the length of the first portions of the wire and thereby move the first portions laterally of the catheter wall into proximity with the catheter wall.

21. The method recited in claim 20 further comprising the step of providing the catheter with a balloon disposed between the wire and the catheter wall, the balloon being inflatable to move the wire into proximity with the body tissue.

22. The method recited in claim 21 wherein the first moving step includes the step of inflating the balloon through the lumen of the catheter wall.

23. The method recited in claim 22 wherein the second moving step includes the step of deflating the balloon through the lumen of the catheter wall.

24. The method recited in claim 21 further comprising the step of attaching the first end of the wire to the catheter distally of the balloon.

25. The method recited in claim 21 further comprising the step of attaching the first end of the wire to the catheter wall proximally of the balloon.

26. A catheter assembly adapted for use in the urinary system and comprising in combination:

an elongate tubular body having a lumen and an axis extending to a distal end;

a dilatable member having an outwardly facing exterior surface and being disposed to surround the distal end of the tubular body in communication with the lumen of the tubular body, the dilatable member being adapted for disposition in the urinary system and being dilatable in response to fluid pressure in the lumen of the tubular body to exert pressure on surrounding body tissue in order to create tension in the body tissue;

cutting means disposed substantially only axially to extend in close contacting relationship with the exterior surface of the dilatable member and having characteristics for being moved into proximity with the surrounding tissue when the dilatable member is dilated, for incising said tissue axially along the tubular body to relieve the tension in the body tissue and to enlarge the body conduit; and means for electrically energizing the cutting means to permit incision and cauterization of the tissue.

27. The assembly of claim 26 wherein the dilatable member is an inflatable bladder that is adapted to be inflated to a predetermined volume and shape.

28. The assembly of claim 27 wherein the cutting means is permanently affixed to the inflatable bladder.

29. The catheter assembly recited in claim 27 wherein the inflatable bladder is symmetrically disposed around the tubular body and the dilation of the inflatable bladder exerts an uniform tangential tension on the surrounding tissue.

30. The assembly of claim 26 wherein the cutting means is an integral component of the dilatable member.

31. The assembly of claim 26 wherein the cutting means comprises a thin wire.

32. The assembly of claim 26 including an open ended sheath from which the tubular body may be ejected for use and into which the tubular body may be retracted after use.

33. The catheter assembly recited in claim 26 wherein the cutting means comprises a radiofrequency electrosurgical cutting element.

34. A catheter adapted to cut tissue, comprising:

a tube having a longitudinal axis extending between a distal end and a proximal end of the catheter;

cutting means disposed generally at the distal end of the tube for cutting the tissue, the cutting means including only a single axially oriented wire, having no point of intersection with any second cutting wire, the single wire having portions movable radially of the axis of the catheter;

means for moving the cutting means portions radially into close proximity to the tissue to be cut;

means for electrically activating the cutting means to cut the tissue in proximity to the cutting means; and means for exposing previously uncut tissue to the cutting means.

35. The catheter recited in claim 34 wherein the moving means comprises a balloon inflatable through the tube and having portions disposed in a fixed relationship with the tube of the catheter.

36. The catheter recited in claim 35 wherein the balloon has a longitudinal axis generally aligned with the longitudinal axis of the tube.

37. The catheter recited in claim 35 wherein the balloon has an outer surface and the wire is movable radially with the outer surface when the balloon is inflated.

38. The catheter recited in claim 34 wherein the exposing means includes means operable with the tube stationary relative to the tissue for applying a force to the tissue to separate the cut tissue and thereby move the uncut tissue into proximity with the cutting means.

39. The catheter recited in claim 38 wherein the exposing means includes a balloon inflatable through the tube and having a curved outer surface, and the force is applied to the tissue tangentially of the outer surface of the balloon.

40. The catheter recited in claim 34 further comprising tamponade means for applying pressure to the cut tissue.

41. The catheter recited in claim 34 wherein the activating means comprises means for directing an electrosurgical signal through the wire, the signal having a magnitude sufficient to cut the tissue.

42. A catheter adapted to cut tissue, comprising:

a tube having a longitudinal axis extending between a distal end and a proximal end of the catheter;

cutting means disposed generally at the distal end of the tube for cutting the tissue, the cutting means including only a single axially oriented wire having no point of intersection with any second cutting wire, the single wire having portions movable radially of the axis of the catheter;

means for moving the cutting means portions radially into close proximity to the tissue to be cut, comprising a balloon inflatable through the tube and having portions disposed in a fixed relationship with the tube of the catheter, the balloon having an outer surface and the wire being movable radially with the outer surface when the balloon is inflated, the balloon having first and second ends fixed to the tube, and the wire having a first end fixed relative to the first end of the balloon and a second end movable relative to the second end of the balloon; and means for activating the cutting means to cut the tissue in proximity to the cutting means; and means for exposing previously uncut tissue to the cutting means.

43. The catheter recited in claim 42 wherein the wire has a proximal end and a distal end and the first end of the wire is the distal end of the wire.

44. Apparatus for cutting a non-vascular body conduit comprising:

a supporting structure having an outer surface;

an electrosurgical cutter in the form of a wire having first portions disposed in a fixed relationship with the supporting structure and second portions disposed outwardly of the outer surface in a movable relationship with the supporting structure;

means disposed between the supporting structure and the second portions of the cutter for moving the second portions of the cutter into proximity with the tissue to be cut; and means for electrically activating the cutter to cut the non-vascular body conduit.

45. The apparatus recited in claim 44 wherein the supporting structure defines a lumen and the moving means comprises a balloon inflatable through the lumen and having first portions fixed to the catheter and second portions movable relative to the catheter, the second portions of the balloon being disposed between the catheter and the second portions of the cutter to move the cutter into proximity with the non-vascular body conduit when the balloon is inflated.

46. Tissue cutting apparatus, comprising:

a supporting structure including portions defining a lumen and having an outer surface;

an electrosurgical cutter in the form of a wire having first portions disposed in a fixed relationship with the supporting structure, and second portions disposed outwardly of the outer surface in a movable relationship with the supporting structure;

means disposed between the supporting structure and the second portions of the cutter for moving the second portions of the cutter into proximity with the tissue to be cut, the moving means comprising a balloon inflatable through the lumen of the supporting structure;

means for electrically activating the cutter to cut the tissue; and means disposed between the cutter and the balloon for directing energy from the electrical cutter away from the balloon and toward the tissue.

47. The tissue cutting apparatus recited in claim 46 wherein the supporting structure is a catheter having a proximal end and a distal end, and the electrosurgical cutter is disposed near the distal end of the catheter.

48. The apparatus recited in claim 47 wherein the supporting structure defines a lumen and the moving means comprises a balloon inflatable through the lumen and having first portions fixed to the catheter and second portions movable relative to the catheter, the second portions of the balloon being disposed between the catheter and the second portions of the cutter to move the cutter into proximity with the tissue when the balloon is inflated.

49. The apparatus recited in claim 48 wherein the first portions of the balloon include first and second ends of the balloon fixed to the catheter, and the second portions of the balloon include a central region movable relative to the catheter to move the cutter outwardly from the catheter into proximity with the tissue.

50. The apparatus recited in claim 48 further comprising:

means for inflating the balloon to move the cutter into proximity with the tissue to be cut; and means for deflating the balloon after the tissue has been cut.

51. The apparatus recited in claim 46 wherein the electrical cutter includes a wire and the directing means includes insulation disposed along the wire between the wire and the balloon.

52. The apparatus recited in claim 51 wherein the insulation forms a sleeve around the wire and portions of the sleeve are removed along the wire to direct the energy toward the tissue.

53. The apparatus recited in claim 46 wherein:

the cutter comprises a wire disposed to extend generally longitudinally of the catheter along the balloon;

the first portions of the cutter include a first end of the wire disposed in a fixed relationship with the catheter; and, the second portions of the cutter include a second end of the wire disposed in a movable relationship with the catheter.

54. A catheter having a longitudinal axis extending between a proximal end of the catheter and a distal end of the catheter, comprising:

a catheter body defining a lumen and a hole extending from the lumen exteriorly of the catheter;

an elongate cutting element in the form of a wire having a distal end with a fixed relationship to the catheter body, a proximal end extending through the hole into the lumen, and intermediate portions disposed between the proximal end and distal end of the wire; and means for moving the proximal end of the wire towards the distal end of the wire for advancing the intermediate portions of the wire laterally of the axis of the catheter.

55. The catheter recited in claim 54 further comprising means for maintaining a tensile force on the cutting element.

56. The catheter recited in claim 55 wherein the maintaining means comprises a tension spring with first portions having a fixed relationship with the catheter and second portions having a fixed relationship with the second end of the cutting element.

57. The catheter recited in claim 56 wherein portions of the catheter define a lumen and the spring is disposed in the lumen of the catheter.

58. The catheter recited in claim 55 wherein operation of the advancing means provides the cutting element with different configurations each of which has the general shape of a parabola.

59. The catheter recited in claim 54 wherein the advancing means comprises a balloon with properties for being inflated and deflated, and the catheter further comprises:

means for inflating the balloon to advance the cutting element;

means for deflating the balloon; and means for automatically retracting the cutting element in response to deflation of the balloon.

60. A catheter having a longitudinal axis extending between a proximal end of the catheter and a distal end of the catheter, comprising:

a catheter body defining a lumen and a hole extending from the lumen exteriorly of the catheter;

an elongate cutting element in the form of a wire having a proximal end with a fixed to the catheter body, a distal end extending through the hole into the lumen, and intermediate portions disposed between the proximal end and distal end of the wire; and means for moving the distal end of the wire toward the proximal end of the wire for advancing the intermediate portions of the wire laterally of the axis of the catheter.

61. A catheter assembly comprising in combination:

an elongate tubular body having a lumen and an axis extending to a distal end;

a dilatable member having an outwardly facing exterior surface and being disposed to surround the distal end of the tubular body in communication with the lumen of the tubular body, the dilatable member being adapted for disposition in the urinary system and being dilatable in response to fluid pressure in the lumen of the tubular body to exert pressure on surrounding body tissue in order to create substantially circumferentially uniform tension in the body tissue;

cutting means comprising a wire and being disposed to extend substantially only axially along at least one half of the length of the dilatable member, and having characteristics for being moved into proximity with the surrounding tissue when the dilatable member is dilated, for incising said tissue along the tubular body to relieve the tension in the body tissue and to enlarge the body conduit.

62. The assembly of claim 61 including means for electrically energizing the cutting means to permit incision and cauterization of the tissue.

63. A catheter having a longitudinal axis extending between a proximal end of the catheter and a distal end of the catheter, comprising:

a catheter body defining a lumen and a hole extending from the lumen exteriorly of the catheter;

an elongate cutting element, at least a portion of which is always disposed exteriorly of the catheter body, said cutting element having a proximal end with a fixed relationship with the catheter body, a distal end extending through the hole into the lumen, and intermediate portions disposed between the proximal end and distal end of the cutting element; and means for moving the distal end of the cutting element toward the proximal end of the cutting element for advancing the intermediate portions of the cutting element laterally of the axis of the catheter.

64. Tissue cutting apparatus, comprising:

a supporting structure having an outer surface;

an electrosurgical cutter in the form of a wire having first portions disposed in a fixed relationship with the supporting structure and second portions disposed outwardly of the outer surface in a movable relationship with the supporting structure, at least a portion of said second portions of the wire being disposed exteriorly of the supporting structure at all times;

means disposed between the supporting structure and the second portions of the cutter for moving the second portions of the cutter into proximity with the tissue to be cut; and means for electrically activating the cutter to cut the tissue.

* * * * *